| United States Patent [19] | [11] Patent Number: 4,605,555 |
| Sato et al. | [45] Date of Patent: Aug. 12, 1986 |

[54] COMPOSITION AND METHOD FOR TREATING KERATOSIC DISORDER OF SKIN AND MUCOSA

[75] Inventors: Mitsunobu Sato, Tokushima; Yasuhiro Katsuragi, Toyonaka; Yasuo Sakano, Amagasaki; Kunio Sugihara, Otsu; Kenji Aimoto, Toyonaka, all of Japan

[73] Assignee: Sun Star Kabushiki Kaisha, Takatsuki, Japan

[21] Appl. No.: 652,465

[22] Filed: Sep. 20, 1984

[51] Int. Cl.⁴ .............................................. A61K 45/02
[52] U.S. Cl. ........................................ 424/85; 530/351
[58] Field of Search ....................... 260/112 R; 424/85

[56] References Cited

U.S. PATENT DOCUMENTS 4,460,574 7/1984 Yabrov .................................... 424/85
4,462,940 7/1984 Hanisch et al. ................. 260/112 R

FOREIGN PATENT DOCUMENTS 0080879 6/1983 European Pat. Off. .............. 424/85
WO01198 4/1983 PCT Int'l Appl. .

OTHER PUBLICATIONS

Chem. Abstracts, vol. 99, 1983, effective date Jun. 8, 1983, Hasegawa et al., 76904n.
Chem. Abstracts, vol. 99, 1983, effective date Apr. 14, 1983, Berg et al., 43554n.

Primary Examiner—Howard E. Schain
Attorney, Agent, or Firm—Wegner & Bretschneider

[57] ABSTRACT

A pharmaceutical composition for treating keratosic disorders of skin and mucosa, particularly, lichen planus and leukoplakia, by topical or local administration which comprises an effective amount of human interferon, a trihydric or more higher polyhydric sugar alcohol, an organic acid buffer and, optionally, an anionic surfactant and albumin, and a conventional pharmaceutical carrier or diluent. A method for treating a human subject suffering from keratosic disorders of skin and mucosa by using this composition is also provided.

9 Claims, No Drawings

COMPOSITION AND METHOD FOR TREATING KERATOSIC DISORDER OF SKIN AND MUCOSA

FIELD OF INVENTION

The present invention relates to a composition and a method for treating keratosic disorders of skin and mucosa. More particularly, it relates to a pharmaceutical composition for treating keratosic disorders of skin and mucosa such as lichen planus and leukoplakia by topical or local application which contains as an active ingredient interferon and a method for treating such disorders using the composition.

BACKGROUND OF INVENTION

Interferon was firstly found as a material produced by living cells for inhibiting growth of virus. Since then, various studies on activities of interferon have been done and it has become clear that interferon has various aspects of biological activities. Further, according to recent technical progress, a large scale production of interferon derived from human cells or human interferon gene-recombining microbial cells and purification thereof for clinical application have become possible. Therefore, clinical application of human interferon in treatment of herpetic keratitis, hepatitis B, viral verruca, brain tumor, skin melanoma and the like has been promoted.

However interferon is a fairly unstable material. Particularly, purified clinically applicable human interferon readily decreases its activity and is readily inactivated by an elevated temperature or mechanical pressure. Accordingly, clinical application of interferon is mainly performed by using lyophilized human interferon and reconstituting it with physiological saline, distilled water or the like to form an injection solution or eye drop when it is administrated.

In order to obtain a stable interferon-containing pharmaceutical composition, various attempts have been done in the prior art. For example, International Application No. WO 83/01198 (PCT/DK82/00092) discloses an interferon-containing gel composition suitable for topical application which includes a polyhydric sugar alcohol, carboxymethyl cellulose, human albumin and a phosphate buffer and a method for treating a human patient suffering from interferon-susceptible disorders such as pre-cancerous or cancerous tumors or local virus infections such as Herpes simplex virus infections or other disorders such as dermatitis, e.g. seborrhea, etc.

Japanese Patent Laid Open Publication No. 92619/1983 discloses that a stable pharmaceutical composition suitable for topical application containing as an active ingredient interferon can be prepared by incorporating interferon with a trihydric or higher polyhydric sugar alcohol and an organic acid buffer. This Publication generically discloses that the composition is effective for treating viral diseases.

Japanese Patent Laid Open Publication No. 167520/1983 discloses that an anionic surfactant can be used as a stabilizer in an interferon-containing composition. This Publication also generically discloses that the composition is effective for treating viral diseases.

The present inventors have surprisingly found that topical or local application of an interferon-containing composition such as that disclosed in the above Japanese Patent Laid Open Publications is effective for treatment of a human subject suffering from keratosic disorders of skin and mucosa such as lichen planus and leukoplakia.

Since causes of keratosic disorders of skin and mucosa are unknown, treatment thereof is performed by, for example, administrating vitamins, adrenal cortex steroids and the like. However, such a conventional method for treating the disorders is insufficient and it is requested to find out an effective method for treating the disorders. On the other hand, none of the prior art including the above International Application and Japanese Patent Laid Open Publication teaches or suggests that interferon is effective for treatment of keratosic disorders of skin and mucosa.

One object of the present invention is to provide a stable interferon-containing pharmaceutical composition for treating keratosic disorders by topical or local application.

Another object of the present invention is to provide a novel method for treating keratosic disorders.

These objects as well as other objects and advantages of the present invention will become apparent to those skilled in the art from the following description.

SUMMARY OF INVENTION

According to the present invention, there is provided a pharmaceutical composition for treating keratosic disorders of skin and mucosa by topical administration which comprises an effective amount of human interferon, and as stabilizers a trihydric or higher polyhydric sugar alcohol and an organic acid buffer, and a conventional pharmaceutical carrier or diluent. Optionally, in addition to the sugar alcohol and the organic acid buffer, the composition of the present invention can further contain as a stabilizer a material selected from the group consisting of anionic surfactants, albumin and combinations thereof.

Further, the present invention provides a method for treating a human subject suffering from keratosic disorders of skin and mucosa such as lichen planus and leukoplakia by using the above composition of the present invention.

In the present invention, keratosic disorders of skin and mucosa can be effectively treated by simply externally applying interferon to a surface of a lesional area such as a surface of skin or mucous membrane including that in oral cavity and the like.

DETAILED EXPLANATION OF INVENTION

Interferon to be formulated as the active ingredient in the composition of the present invention can be any interferon derived from human being. For example, there can be used human interferon prepared by using human leukocytes or normal human diploid cells according to a known technique, human interferon derived from human interferon gene-recombining microbial cells prepared according to a known recombination DNA technique or human interferon prepared by using a known cellfusion technique. The amount of interferon to be formulated in the composition is not limited to a specific range and can be appropriately chosen based on a desired effect, a particular form of the composition and the like. However, in view of the effect, it is generally preferable to formulate human interferon having the specific activity of $1 \times 10^5$ international units (IU)/mg protein or more in such an amount that 100 g of the composition contains $1 \times 10^4$ IU or more of interferon.

Examples of the trihydric or higher polyhydric sugar alcohol to be used as the stabilizer in the present invention include glycerin, erythritol, arabitol, xylitol, sorbitol, mannitol and the like. These polyhydric sugar alcohols can be used alone or in a combination thereof. In view of the stabilization of interferon, the sugar alcohol is formulated in an amount of 15% by weight or more, preferably, 25 to 70% by weight based on the composition.

The organic acid buffers to be used as the stabilizer in the present invention can be conventional buffers of organic acids and salts thereof. Examples thereof include citrate buffers (e.g. monosodium citrate-disodium citrate mixture, citric acid-trisodium citrate mixture, citric acid-monosodium citrate mixture, etc.); succinate buffers (e.g. succinic acid-monosodium succinate mixture, succinic acid-sodium hydroxide mixture, succinic acid-disodium succinate mixture, etc.); tartrate buffers (e.g. tartaric acid-sodium tartrate mixture, tartaric acid-potassium tartrate mixture, tartaric acid-sodium hydroxide mixture, etc.); fumarate buffers (e.g. fumaric acid-monosodium fumarate mixture, fumaric acid-disodium fumarate mixture, monosodium fumarate-disodium fumarate mixture, etc.); gluconate buffers (e.g. gluconic acid-sodium gluconate mixture, gluconic acid-sodium hydroxide mixture, gluconic acid-potassium gluconate mixture, etc.); oxalate buffers (e.g. oxalic acid-sodium oxalate mixture, oxalic acid-sodium hydroxide mixture, oxalic acid-potassium oxalate mixture, etc.); lactate buffers (e.g. lactic acid-sodium lactate mixture, lactic acid-sodium hydroxide mixture, lactic acid-sodium hydroxide mixture, lactic acid-potassium lactate mixture etc.) and acetate buffers (e.g. acetic acid-sodium acetate mixture, acetic acid-sodium hydroxide mixture, etc.). In view of the stabilization of interferon, it is desirable to formulate the organic acid buffer in an amount of 0.01 mole/kg composition or more, preferably, 0.1 to 0.2 mole/kg composition so as to adjust the pH of the composition to 3 to 6.

Examples of the anionic surfactants include sodium alkyl sulfates, the alkyl groups of which have 8 to 18 carbon atoms (e.g. sodium lauryl sulfate, sodium oleyl sulfate, etc.); sodium polyoxyethylene alkyl ether sulfates average number of moles of ethylene oxide added of which are 2 to 4 and alkyl groups of which having 8 to 18 carbon atoms (e.g. sodium polyoxyethylene lauryl ether sulfate, sodium polyoxyethylene oleyl ether sulfate, etc.) and sodium alkyl sulfosuccinates alkyl groups of which have 8 to 18 carbon atoms (e.g. sodium lauryl sulfosuccinate, sodium oleyl sulfosuccinate, etc.). The anionic surfactants can be used alone or in a combination thereof and are formulated in an amount of 0.008% by weight or more, preferably, 0.05% to 4% by weight or more, particularly, 0.1 to 1% by weight based on the composition.

Examples of albumin are human serum albumin, bovine serum albumin, ovalbumin and a mixture thereof. Albumin is formulated in an amount of 0.01 to 1% by weight based on the composition.

The pharmaceutical carrier or diluent to be used in the present invention can be solid or liquid. For example, there can be used waxes, cellulose derivatives, carboxyvinyl polymers and water. In case of a solid composition, it is preferable to use sodium carboxymethyl cellulose as a carrier or binder because it does not adversely effect on the activity of interferon.

The composition of the present invention can be prepared in a conventional form suitable for topical or local application such as an ointment, a paste, a gel, a spray, a liquid and the like by incorporating the stabilizers and the carrier or diluent with interferon according to a known technique. In order to avoid decrease of the activity of interferon during the production steps of the composition, it is preferable to add interferon to a mixture of remaining ingredients at the end step.

The method for treating a human subject suffering from keratosic disorders of skin and mucosa of the present invention is performed by topically applying the composition of the present invention to a surface of a lesional area such as a surface of skin or mucous membrane including that in an oral cavity and the like according to a known manner. It is preferable to cover the applied area with a bandage, plaster, tape or the like to prevent removal of interferon from the lesional area and to accelerate absorption of interferon to enhance therapeutic effect. Particularly, when the composition is applied to a lesional area on the mucous membrane in oral cavity, the therapeutic effect is enhanced by using an adhesive tape for mucous membrane in an oral cavity (e.g. that disclosed in Japanese Patent Laid Open Publication No. 128314/1983) to prevent removal of interferon by saliva or movement of the tongue.

In the method of the present invention, it is preferable to apply the composition containing 10 to $10^8$ IU of interferon per single dosage for an adult human subject. For example, when the gel composition of the present invention containing $10^4$ to $10^9$ IU of interferon/100 g of the composition or the ointment of the present invention containing $10^5$ to $10^{10}$ IU of interferon /100 g of the composition is used, 0.01 to 10 g of the composition per single dosage can be applied by the finger, a spatula and the like depending upon the size of the lesional area. The composition can be applied 1 to 3 times per day.

The following Examples and Experiments further illustrate the present invention in detail but are not to be construed to limit the scope thereof. Interferon used in the Examples and Experiments was obtained from fibroblasts derived from human prepuce, which met the standard for clinical application ruled by the National Institute of Health in Japan based on purity, yield and the like and satisfied the safety requirement in the preclinical test requested by Japanese Ministry of Public Welfare.

EXAMPLE 1

| Ingredients | % by weight |
| --- | --- |
| Sodium lauryl sulfate | 0.2 |
| Carboxymethyl cellulose | 2.0 |
| Glycerin | 40.0 |
| 0.4 mole/l Citrate buffer (pH 4.5) | 25.0 |
| Distilled water to | 100 |

An interferon-containing gel composition for topical application was prepared by mixing the above ingredients to obtain a base and then mixing the base with human interferon in the amount of $1 \times 10^7$ IU per 100 g of the base.

EXAMPLE 2

Gel Composition Base Formulation

| Ingredients | % by weight |
| --- | --- |
| Carboxymethyl cellulose | 2.0 |
| Glycerin | 45.0 |

| -continued | |
|---|---|
| Ingredients | % by weight |
| 0.4 mole/l Citrate buffer (pH 4.5) | 25.0 |
| Distilled water to | 100 |

An interferon-containing gel composition for topical application was prepared by mixing the above ingredients to obtain a base and then mixing the base with interferon in an amount of $1 \times 10^6$ IU per 100 g of the base.

EXAMPLE 3

Ointment Base Formulation

| Ingredients | % by weight |
|---|---|
| Carboxymethyl cellulose | 0.2 |
| Glycerin | 30.0 |
| Petrolatum album | 20.0 |
| Stearyl alcohol | 22.0 |
| 0.4 mole/l Citrate buffer | 25.0 |
| Distilled water to | 100 |

An interferon-containing ointment was prepared by mixing the above ingredients to obtain a base and then mixing the base with interferon in an amount of $1 \times 10^6$ IU per 100 g of the base.

EXAMPLE 4

Paste Base Formulation

| Ingredients | % by weight |
|---|---|
| Carboxymethyl cellulose | 2.0 |
| Glycerin | 25.0 |
| Cetanol | 2.8 |
| Glyceryl monostearate | 9.3 |
| Tween 80 | 2.0 |
| Glucuronic acid | 1.0 |
| 0.4 mole/l Citrate buffer | 20.0 |
| Distilled water to | 100 |

An interferon-containing paste was prepared by mixing the above ingredients to obtain a base and then mixing the base with interferon in an amount of $1 \times 10^4$ IU per 100 g of the base.

EXAMPLE 5

Liquid Composition Base Formulation

| Ingredients | % by weight |
|---|---|
| Carboxymethyl cellulose | 0.1 |
| Glycerin | 15.0 |
| 0.4 mole/l Citrate buffer (pH 4.5) | 50.0 |
| Distilled water to | 100 |

An interferon-containing liquid composition was prepared by mixing the above ingredients to obtain a base and then mixing the base with interferon in an amount of $1 \times 10^5$ IU per 100 g of the base.

EXAMPLE 6

Spray Composition Formulation

| Ingredients | % by weight |
|---|---|
| The liquid composition of Example 5 | 50.0 |

| -continued | |
|---|---|
| Ingredients | % by weight |
| Freon 114 | 50.0 |

An interferon-containing spray composition was prepared by filling the liquid composition together with Freon 114 into a 50 ml Teflon-coated aluminum container.

Safety Tests (1) Primary Skin Irritation Test

Each gel composition obtained in Examples 1 and 2 was applied on each shaved back of 6 female New Zealand White rabbits (body weight: 2.5 to 3.0 kg) and each applied area was closely covered for 24 hours. Then, the gel composition was removed and, after 30 minutes, the applied area was observed. However, no abnormality was observed.

(2) Skin Sensitization Test

According to intra-dermal injection sensitization method, each gel composition obtained in Examples 1 and 2 was tested by using 23 female Hartley white guinea pigs (body weight: 300 to 350 g). As the result, except the effect of human serum albumin which had been added to the interferon used as a stabilizer, no sensitization was observed. Further, although a closely covered 24 hour patch test of the gel composition was carried out, no positive result was observed.

(3) Human Patch Test

A closely covered 24 hour patch test of each gel composition obtained in Examples 1 and 2 was carried out on the back of 10 healthy adult men. Then, the gel composition was removed and, after 60 minutes, the test area was observed. However, no abnormality was observed.

(4) Human Oral Mucosa Irritation Test

Each gel composition obtained in Examples 1 and 2 was applied on each oral mucosa of 8 healthy adult men and covered with the above described adhesive tape for oral mucosa. After 60 minutes, the tape was removed and the test area was observed. However, no abnormality was observed.

CLINICAL TESTS (1) Treatment of lichen planus

Patient: female, 73 years old

At the first medical examination, reddening lesional areas accompanying broad edema were observed on the buccal mucosa of both sides and presence of lacy white streak and white coating were partly observed. According to the clinical observation as well as a pathological diagnosis of the tissue, it was determined as lichen planus.

Firstly, treatment was performed by administrating Vitamins A, B complex and C. However, the condition of the disorder was unchanged.

Then, application of the gel composition of Example 1 was commenced. After 4 single doses were applied on 1st, 3rd, 7th and 12th days from the commencement of application, respectively, the reddening lesion was somewhat increased but the lesional areas began to localize and was clearly distinguished from the surrounding mucosa. Further, the gel composition was applied on 22nd, 36th, 43rd, 48th, 57th and 62nd days. After application on 62nd day (10th time application), the lesional areas were reduced. Then, single dose application was repeated three times and treatment was terminated. At that time, the lesional areas on the oral mucosa almost completely disappeared. No relapse was observed.

(2) Treatment of lichen planus
Patient: female, 51 years old

At the first medical examination, reddening lesion of oral mucosa and presence of erosion, ulcer, white coating and white streak were observed at the site from the mandibular buccal gingiva to the distomolar gingiva of both sides as well as at buccal mucosa around the opening of Stensen's duct. According to both the clinical observation and the pathological diagnosis of the tissue, it was determined as lichen planus. Then, application of the gel composition of Example 1 was commenced together with antiphlogistic treatment. 4 Single doses were applied on 1st, 3rd, 6th and 10th days, respectively, after commencement of application. Since then, the lesional areas began to be clearly distinguished from the surrounding mucosa but the reddening lesion was increased and became hemorrhagic. Application of the gel composition was further repeated and, after about 7th time application (30th day), Wickham's striae tended to disappear and hemorrhage was mitigated. In addition, the lesional areas were localized and reduced. Until 62nd day, total 12 single doses were applied and the lesional areas on the oral mucosa were reduced. Then, since the condition was fixed, the remaining lesional areas on the oral mucosa were excised and skin transplantation was effected. Mucosa lesion was almost completely healed and no relapse was observed.

(3) Treatment of lichen planus
Patient: male, 73 years old

In order to treat recurrent carcinoma of the buccal mucosa, the patient had undergone the primary focus excision and upper radical neck lymphnode dissection. After that, lichen planus was observed at the site from the left mandibular distomolar gingiva to the buccal mucosa. Then, application of the gel composition of Example 2 was commenced. 3 Single doses were applied on 1st, 5th and 10th days, respectively, from the commencement of application. Since then, reddening and tumor of the lesional area on the mucosa were temporarily increased but, after 7th time application on 25th day, erosion tended to be improved. When application was further continued, the condition was gradually improved. On 62th day, 11th application was effected and the treatment was finished. The lesion was almost completely healed and no relapse was observed.

(4) Treatment of leukoplakia
Patient: female, 63 years old

Leukoderma and erosion were observed on the dorsum of the tongue and application of a steroid ointment was continued. However, no improvement of the condition was observed. Leukoderma and formation of tumor at the site from lingual margin to lingual apex of both sides as well as spontaneous pain were observed. According to the clinical observation and a pathological diagnosis, it was determined as leukoplakia. Then, application of the gel composition of Example 1 was commenced. By 5th time application on 46th day from commencement of application, leukoplakia almost disappeared and no relapse was observed.

(5) Treatment of leukoplakia
Patient: male, 63 years old

At the first medical examination, white lesion area which could not be removed by rubbing (about $2.5 \times 2$ cm) was observed at the site from the lower part of the opening of Stensen's duct to the distomolar on the left buccal mucosa. The surface was partly granular and erosion and edema were present provided that no remarkable tumor formation was observed. According to the clinical observation and a pathological diagnosis, it was determined as leukoplakia. Then, application of the gel composition of Example 1 was commenced. After 4th time application on 19th day from commencement of application, leukoplakia lesional area on the buccal mucosa began to disappear. After 10th time application on 62nd day, only keratosic white streak remained and contact pain was mitigated. Further, erosion and reddening of the mucosa disappeared. In this case, treatment terminated after 10th time application. Although keratosic white streak remained, no subjective symptoms and no relapse were observed.

(6) Treatment of leukoplakia
Patient: female, 70 years old

A lesional area including reddening, erosion and white lesion which could not be removed by rubbing was observed at the site from the right lower lip to the buccal mucosa and about the alveolar gingiva of molar region. According to the clinical observation and a pathological diagnosis of the tissue, it was determined as leukoplakia. Then, application of the gel composition of Example 2 was commenced. After 3rd time application on 27th day from commencement of application, furry tongue gradually disappeared. Further, although reddening of the mucosa was somewhat temporarily increased, it was gradually improved. After 10th time application on 84th day, the leukoplakia lesion almost disappeared and subjective symptoms such as contact pain and the like also disappeared.

During these clinical tests, no abnormal blood count and biochemical values of the patients were observed.

What is claimed is:

1. A method for treating a human subject suffering from lichen planus or leukoplakia which comprises externally applying a pharmaceutical composition comprising an effective amount of human interferon, 15 to 70% by weight of a trihydric of higher polyhydric sugar alcohol, an organic acid buffer and a conventional pharmaceutical carrier or diluent, the pH of the composition being about 3 to 6.

2. A method according to claim 1, wherein the composition is applied in such an amount that 10 to $10^8$ IU of interferon is applied per single dosage.

3. A method according to claim 1, wherein the polyhydric sugar alcohol in the composition is a member selected from the group consisting of glycerin, erythritol, arabitol, xylitol, sorbitol, mannitol and a mixture thereof.

4. A method according to claim 1, wherein the organic acid buffer in the composition is a member selected from the group consisting of citrate buffer, succinate buffer, fumarate buffer, gluconate buffer, oxalate buffer, lactate buffer and acetate buffer and is formulated in an amount of 0.01 to 0.2 mole/kg composition.

5. A method according to claim 1, wherein the composition further includes an anionic surfactant.

6. A method according to claim 5, wherein the anionic surfactant is a member selected from the group consisting of sodium alkyl sulfate the alkyl group of which has 8 to 18 carbon atoms; sodium polyoxyethylene alkyl ether sulfate the average number of mole of ethylene oxide added of which is 2 to 4 and the alkyl group of which has 8 to 18 carbon atoms; sodium alkyl sulfosuccinate the alkyl group of which has 8 to 18 carbon atoms; and a mixture thereof and is formulated in an amount of 0.008 to 4% by weight based on the composition.

7. A method according to claim 1, wherein the composition further includes albumin in an amount of 0.01 to 1% by weight based on the composition.

8. A method according to claim 1, wherein the composition is in the form of a solid and contains as a binder carboxymethyl cellulose.

9. A method according to claim 1, wherein the composition is in the form suitable for application in the oral cavity.

* * * * *